US00PP09291P

United States Patent [19]

Dehan

[11] Patent Number: Plant 9,291

[45] Date of Patent: Sep. 19, 1995

[54] ASTER PLANT NAMED 'SUNSTAR'

[75] Inventor: Klara Dehan, Holon, Israel

[73] Assignee: Danziger-"Dan" Flower, Post Beit Dagan, Israel

[21] Appl. No.: 291,697

[22] Filed: Aug. 16, 1994

[51] Int. Cl.[6] ..... A01H 5/00

[52] U.S. Cl. ..... Plt./68.1

[58] Field of Search ..... Plt. 68.1

*Primary Examiner*—James R. Feyrer

*Attorney, Agent, or Firm*—Foley & Lardner

[57] ABSTRACT

A new and distinct cultivar of aster plant named Sunstar, characterized by its purple ray floret color and deep purple mature discs; relatively small diameter, double flowers; strong and rigid stems, each of which carries many flowers; excellent branching producing a spreading plant shape; early flowering; and excellent flower keeping qualities.

1 Drawing Sheet

The present invention comprises a new and distinct cutivar of Aster plant, botanically known as *Aster ericoides* hereinafter referred to by the cultivar name Sunstar.

The new cultivar was originated from a cross made in a controlled breeding program program by the inventory Klara Dehan in Mishmar Hashiva, Israel.

Both the female, or seed, and the male, or pollen parents were cultivars of *Aster ericoides* the breeding numbers of which were unrecorded and are unknown at this time. Both parents are proprietary lines used exclusively for breeding.

Sunstar was discovered and selected by the inventor as a flowering plant within the progeny of the stated cross in a controlled environment in Mishmar Hashiva, Israel. Asexual reproduction of the new cultivar by leaf cuttings performed by the inventor at Mishmar Hashiva, Israel has demonstrated that the combination of characteristics as herein disclosed for the new cultivar are firmly fixed and retained through successive generations of asexual reproduction.

Sunstar has not been observed under all possible environmental conditions. The phenotype may vary somewhat with variations in environment such as temperature, light intensity and day length, without, however, any variation in genotype. The following observations, measurements and values describe the new cultivar as grown in Mishmar Hashiva, Israel under conditions which closely approximate those generally used in commercial practice.

The following traits have been repeatedly observed and are determined to be basic characteristics of Sunstar which in combination distinguish this aster as a new and distinct cultivar:

1. Unique purple ray floret color.
2. Deep purple disc florets.
3. Rich flowering on many side branches.
4. Excellent branching, producing a spreading plant shape.
5. Early flowering.
6. Can be grown in garden bedding programs or in greenhouse cut spray programs.
7. Excellent flower keeping quality.

The accompanying color photographic drawing illustrates a portion of a typical specimen plant of the new cultivar, with partially open, and completely open flowers being illustrated. The flowers are shown enlarged relative to true size. The true ray and disc floret colors, accurately noted below, are not accurately shown in the photograph.

In the following description, color references are made to the Royal Horticultural Society Colour Chart (RHS), except where general colors of ordinary significance are referred to. Color values were taken in the morning in Mishmar Hashiva, Israel.

Classification:

*Botanical.*—*Aster ericoides* Hybrid cv. Sunstar.

*Commercial.*—Daisy-like spray or garden variety.

Parentage:

*Male parent.*—Unknown seedling of *Aster ericoides.*

*Female parent.*—Unknown seedling of *Aster ericoides.*

Propagation: The new cultivar holds its distinguishing characteristics through successive propagations by leaf cuttings.

INFLORESCENCE

A. Capitulum:

*Form.*—Daisy, round, generally flat.

*Type.*—Double, with petals appearing in 2–4 rows, with approximately 4 rows in winter flowering.

*Diameter across face.*—2–3 cm, depending on the growing season, with the diameter being larger in winter flowering.

B. Corolla of ray florets:

*Color (general tonality from a distance of three meters).*—purple.

*Color (upper surface).*—77A.

*Color (under surface).*—87B.

*Shape.*—Florets are generally narrow and oblong, with apex upwardly rounded; straight to slightly concave. The rounded apex and concave transverse shape provide a cupped appearance as a result of which the flower has a full appearance.

*Size.*—The petals are 7–8 mm in length and 3–4 mm in width, with the width being significantly larger than typical cultivars of the species.

C. Corolla of disc florets:

*Color (mature).*—Deep purple 79A.

*Color (mature).*—Yellow changing to purple.

*Diameter of disc.*—1 cm.

D. Flowering period: When field grown in natural season, plants planted in June will flower in September. In winter greenhouse production, preferred culture includes approximately four weeks of long-day treatment after pinching until the stems elongate to approximately 10 cm, followed by short days. From the start of short days, Sunstar will flower in the fall in approximately 5 weeks, and in the winter in approximately 7 weeks.

E. Reproductive organs:

*Androecium.*—Stamens present on both ray and disc florets and yellow to purple in color; pollen is yellow and found only in the winter season in Israel.

*Gynoecium.*—Present on both disc florets; green in color.

F. Fertility: Has not be ascertained.

G. Receptacle: The receptacle, involucre and phyllaries are normal for plants of this species.

PLANT

A. General appearance: Excellent branching and very heavy stems result in a great abundance of purple flowers; medium to tall in height, with the main stem reaching a height of 0.9 to 1.1 meters in fully grown plants. After repeated crops, base of plant does not become woody.

B. Foliage:

*Color.*—137A.

*Shape.*—Linear, without stipules with occasional downward reflexing at the tip.

*Size.*—Typically, leaves at upper part of plant are 55 mm long and 5 mm wide; leaves in bottom part of plant are larger, being approximately 85 mm in length and 11 mm in width.

*Margin.*—Entire.

*Arangement.*—Alternate, with angle acute.

I claim:

1. A new and distinct cultivar of aster plant named Sunstar, as illustrated and described.

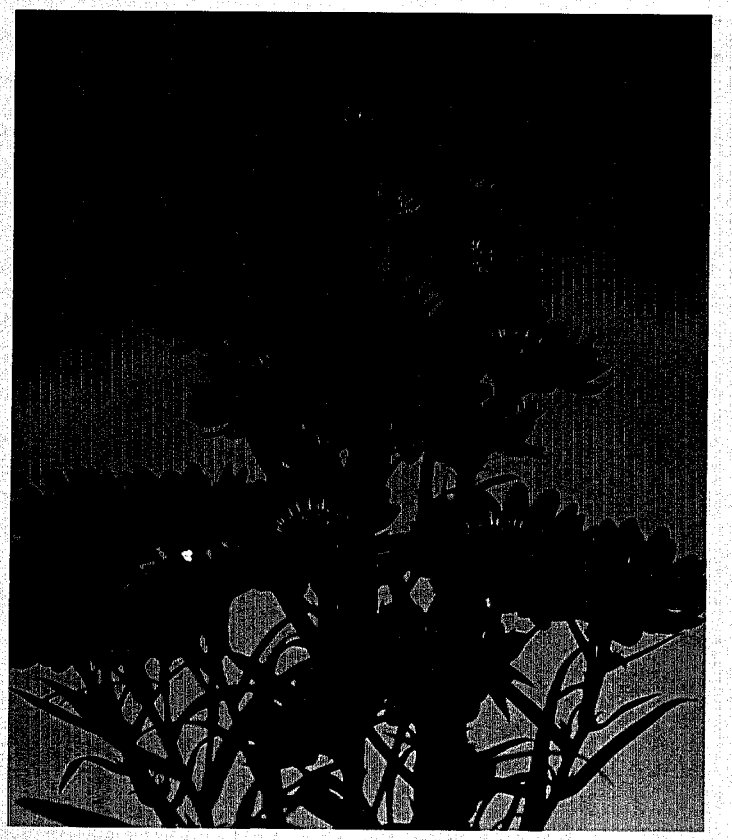

* * * * *